(12) United States Patent
Shaw et al.

(10) Patent No.: US 12,318,598 B2
(45) Date of Patent: Jun. 3, 2025

(54) MEDICAL SYRINGE

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US)

(73) Assignee: Retractable Technologies, Inc., Little Elm, TX (US)

( * ) Notice: Subject to any disclaimer, the term of this patent is extended or adjusted under 35 U.S.C. 154(b) by 878 days.

(21) Appl. No.: 17/518,308

(22) Filed: Nov. 3, 2021

(65) Prior Publication Data

US 2022/0054764 A1 Feb. 24, 2022

Related U.S. Application Data

(63) Continuation-in-part of application No. 16/370,239, filed on Mar. 29, 2019, now Pat. No. 12,064,605, which is a continuation-in-part of application No. 15/940,305, filed on Mar. 29, 2018.

(51) Int. Cl.
*A61M 5/32* (2006.01)
*A61M 5/31* (2006.01)

(52) U.S. Cl.
CPC ........ *A61M 5/3221* (2013.01); *A61M 5/3245* (2013.01); *A61M 2005/3126* (2013.01)

(58) Field of Classification Search
CPC .. A61M 5/31511; A61M 5/321; A61M 5/322; A61M 5/3219; A61M 5/3205; A61M 5/3221; A61M 5/3232; A61M 5/3269; A61M 5/3271; A61M 5/50; A61M 5/178;
(Continued)

(56) References Cited

U.S. PATENT DOCUMENTS

| 4,573,976 A | 3/1986 | Sampson |
| 4,702,738 A | 10/1987 | Spencer |
| 4,790,828 A | 12/1988 | Dombrowski |

(Continued)

FOREIGN PATENT DOCUMENTS

| CN | 102573959 | 7/2012 |
| CN | 108619594 | 9/2018 |

(Continued)

*Primary Examiner* — Laura A Bouchelle
(74) *Attorney, Agent, or Firm* — Scheef & Stone, LLP; Robin L. Barnes; Mike Schofield

(57) ABSTRACT

A safety syringe for medical use having an injection molded plastic body with a tubular barrel, a transverse finger flange surrounding the barrel and two upwardly projecting wings with substantially flat, outwardly facing surfaces disposed forwardly of the finger flange, a plunger assembly slidably engaging an inside wall of the barrel, a needle with a tip projecting forwardly from the barrel, and a needle safety shield slidably engaging the body between the wings, wherein the transverse finger flange has a window that allows core pin insertion through the window during injection molding of the body, the plunger assembly has a proximal end cap that is integral with the plunger handle and abuts a rearwardly facing surface of the transverse finger flange, and the needle safety shield has a distal end with a cylindrical needle guard that is forwardly movable following use of the syringe to guard the needle tip.

20 Claims, 14 Drawing Sheets

(58) Field of Classification Search
CPC .... A61M 2005/314; A61M 2005/3125; A61M 2005/3126; A61M 2005/3227
See application file for complete search history.

(56) References Cited

U.S. PATENT DOCUMENTS

| | | | |
|---|---|---|---|
| 4,840,619 A | 6/1989 | Hughes | |
| 4,915,696 A | 4/1990 | Feimer | |
| 4,946,447 A | 8/1990 | Hardcastle | |
| 5,092,461 A | 3/1992 | Adam | |
| 5,215,534 A | 6/1993 | DeHarde | |
| 5,312,372 A | 5/1994 | DeHarde | |
| D377,687 S | 1/1997 | Udovch | |
| 5,672,161 A | 9/1997 | Allen et al. | |
| D420,129 S | 2/2000 | McMahon | |
| 6,090,077 A | 7/2000 | Shaw | |
| 6,213,987 B1* | 4/2001 | Hirsch | A61M 5/3269 604/263 |
| 6,416,323 B1 | 7/2002 | Grenfell et al. | |
| 6,585,690 B1 | 7/2003 | Hoeck | |
| 8,372,044 B2 | 2/2013 | Westbye | |
| 8,496,627 B2* | 7/2013 | Chelak | A61M 5/326 604/198 |
| D693,003 S | 11/2013 | Wang | |
| 9,044,552 B2 | 6/2015 | Schraga | |
| 9,173,726 B2 | 11/2015 | Sabourin | |
| 9,623,192 B2 | 4/2017 | Chin | |
| D792,969 S | 7/2017 | Taylor | |
| D894,381 S | 8/2020 | Shaw et al. | |
| D914,872 S | 3/2021 | Shaw et al. | |
| 11,246,989 B1* | 2/2022 | Halbach | A61M 5/46 |
| 12,064,605 B2* | 8/2024 | Shaw | A61M 5/3234 |
| 2002/0065488 A1 | 5/2002 | Suzuki | |
| 2002/0068907 A1 | 6/2002 | Dysarz | |
| 2003/0028171 A1 | 2/2003 | DeHarde | |
| 2005/0159706 A1 | 7/2005 | Wilkinson | |
| 2006/0264825 A1 | 11/2006 | Westbye et al. | |
| 2008/0114306 A1 | 5/2008 | Bare | |
| 2012/0004621 A1 | 1/2012 | Shaw | |
| 2013/0023826 A1 | 1/2013 | Ishida | |
| 2014/0012206 A1 | 1/2014 | Shaw | |
| 2015/0196714 A1 | 7/2015 | Creaturo | |
| 2015/0202373 A1 | 7/2015 | Creaturo | |
| 2015/0231335 A1 | 8/2015 | Creaturo | |
| 2019/0298929 A1* | 10/2019 | Shaw | A61M 5/3129 |
| 2023/0034986 A1 | 2/2023 | Shaw et al. | |
| 2024/0075216 A1 | 3/2024 | Shaw et al. | |
| 2024/0165337 A1 | 5/2024 | Shaw et al. | |
| 2024/0165341 A1 | 5/2024 | Shaw et al. | |

FOREIGN PATENT DOCUMENTS

| | | |
|---|---|---|
| DE | 4323466 A1 | 1/1994 |
| JP | 200295746 | 2/2010 |
| WO | 2016176523 A1 | 11/2016 |

* cited by examiner

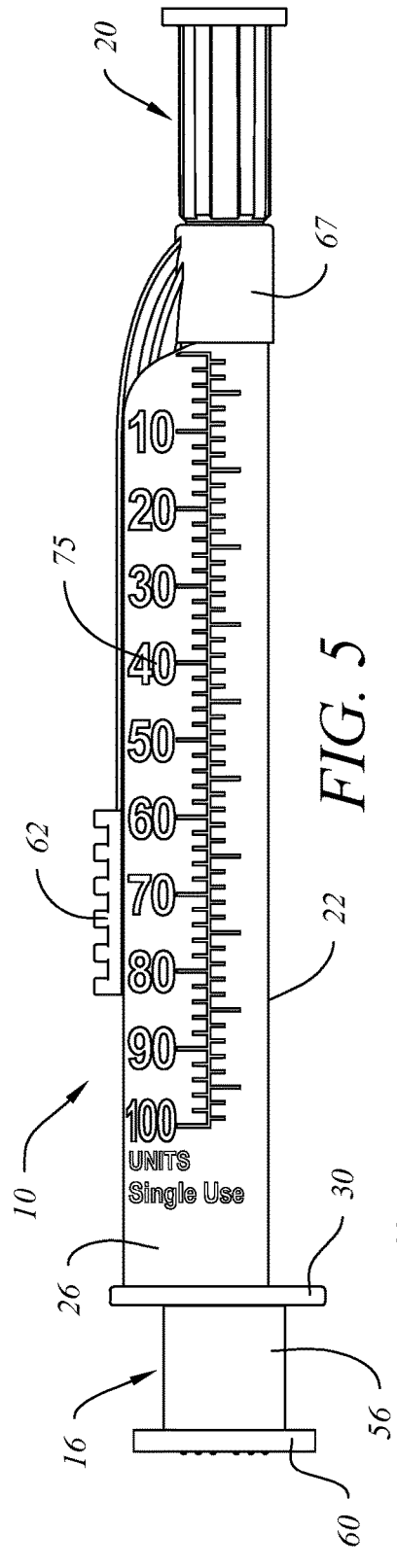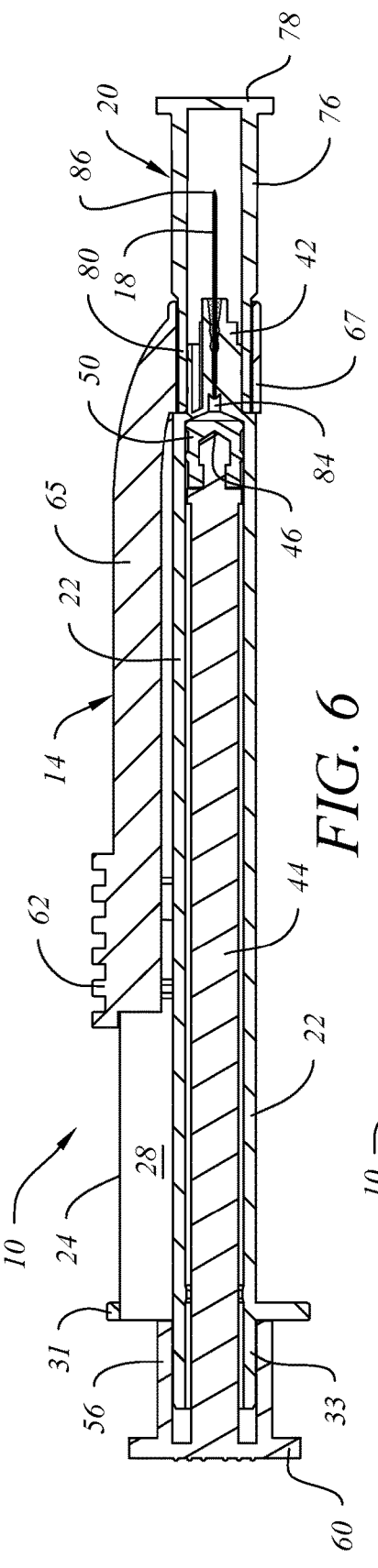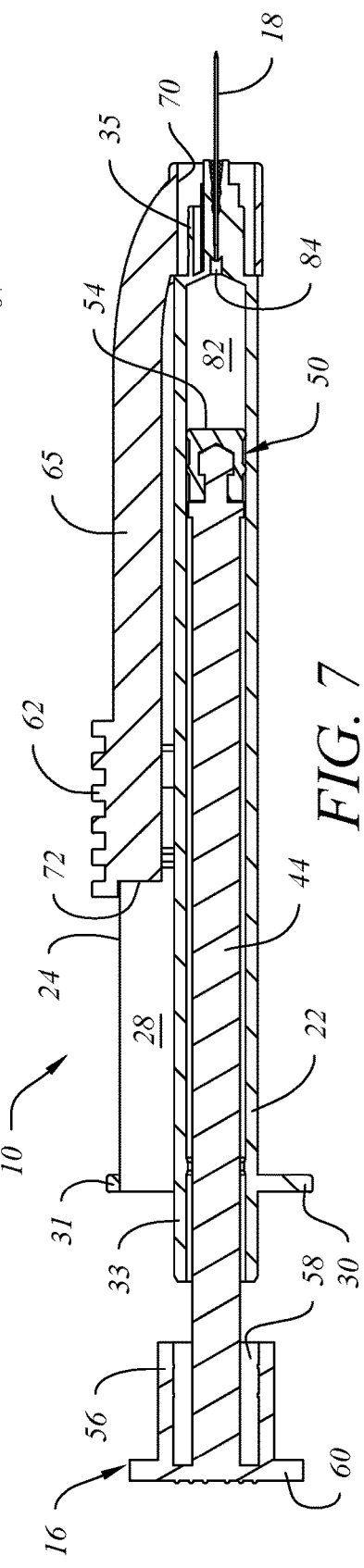

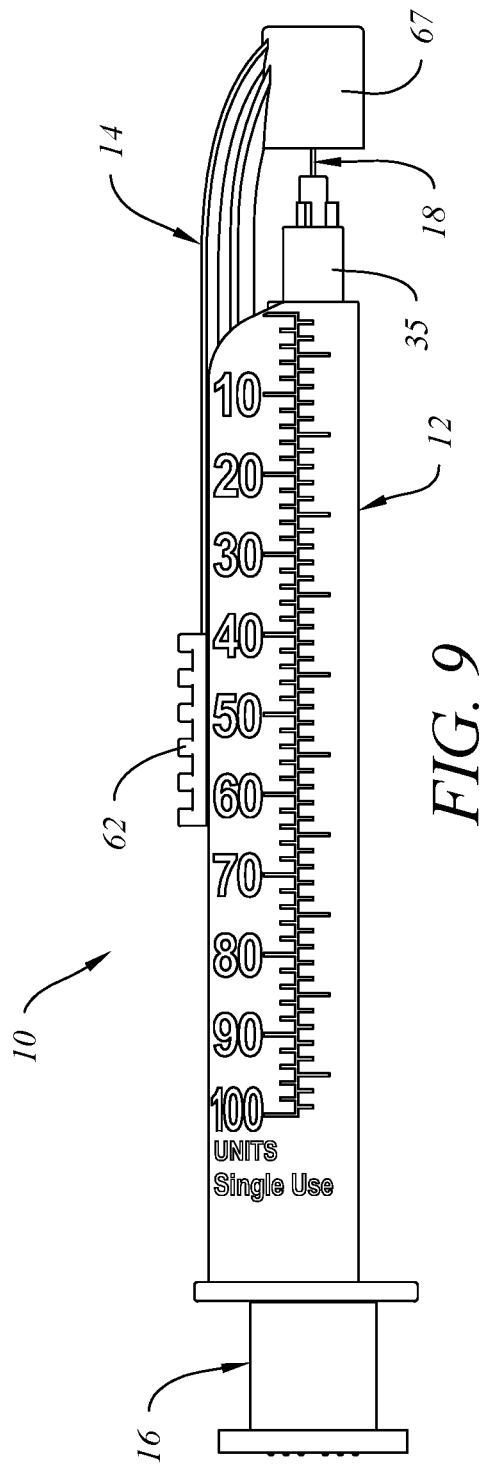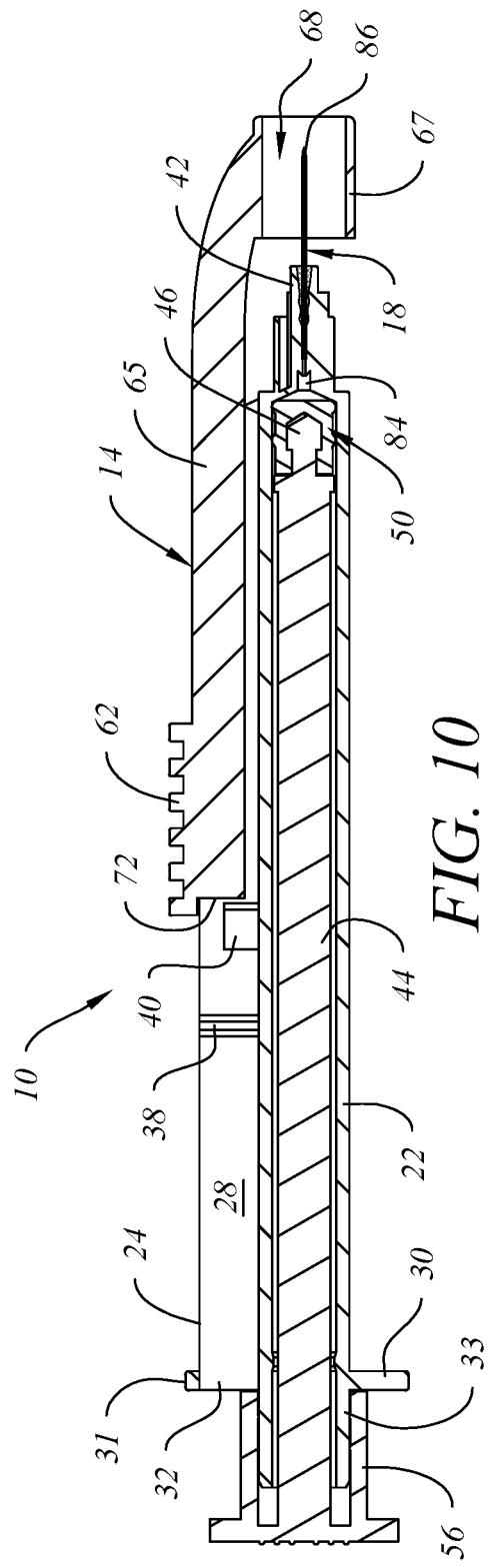

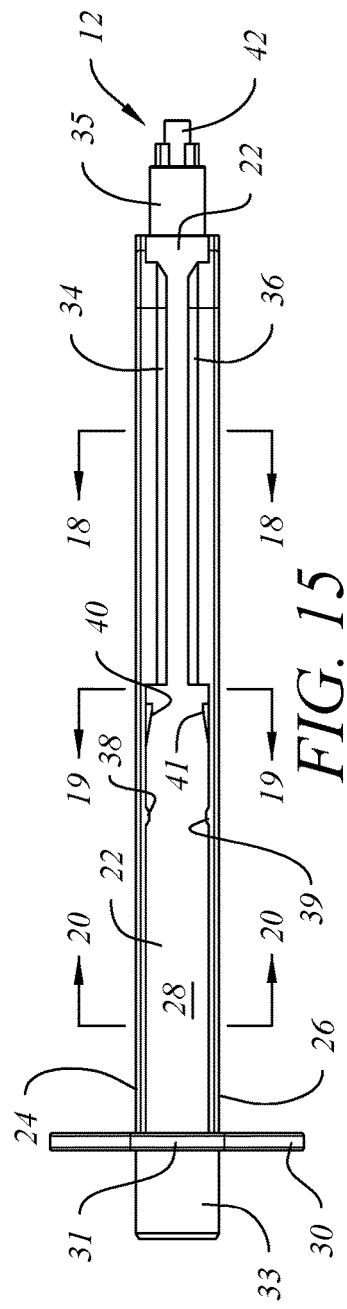
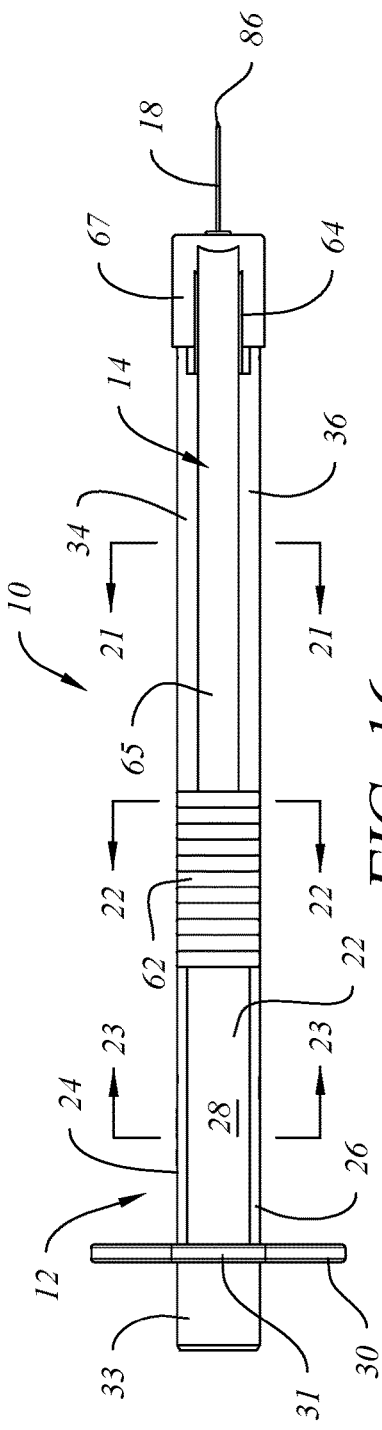
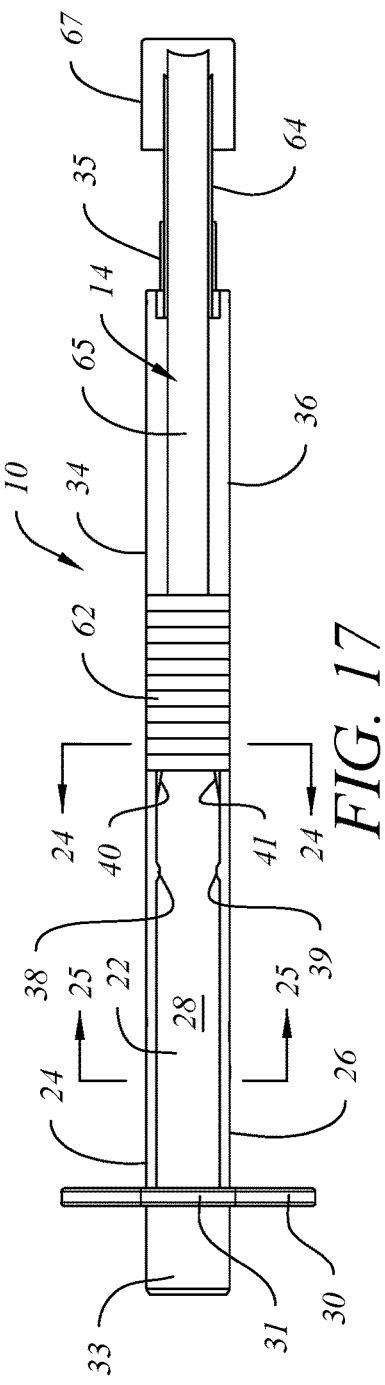

MEDICAL SYRINGE

CROSS-REFERENCE TO RELATED APPLICATIONS

This application is a continuation-in-part of U.S. application Ser. No. 16/370,239, filed Mar. 29, 2019, which is a continuation-in-part of application Ser. No. 15/940,305, filed Mar. 29, 2018.

BACKGROUND OF THE INVENTION

1. Field of the Invention

This invention relates to a safety syringe configured for medical use in aspirating or injecting fluids that does not comprise a retractable needle. As used here, the term "safety syringe" refers to a syringe having one or more structures and/or protection features that function or cooperate to reduce the likelihood that a user or subsequent handler of the device, a patient or a bystander will experience an inadvertent, accidental or unintended needle stick from a needle or cannula that is part of or used in association with the subject device.

2. Description of Related Art

Syringes intended for medical use are typically made with removable plunger caps that help prevent contaminants from entering a syringe barrel through the annular space that otherwise exists around the plunger handle at the rear of the barrel prior to use of the device. Such plunger caps are typically removed and disposed of prior to use. A safety syringe is needed that does not require the production, use or disposal of a plunger cap that is removable prior to use of the device.

Syringes intended for medical use are typically made with barrels comprising substantially cylindrical inside and outside walls, meaning that volumetric dosage indicia or other markings are applied to an arcuate outer surface during manufacture. This can be difficult, and especially when the diameter of the barrel and radius of curvature of the outside wall are small (as with 1 mL, 0.5 mL and smaller syringes) and where the available outside surface area is extremely limited, or on syringes where different dosing scales or other indicia are applied to opposite sides of the barrel. In such instances it is often necessary to spin or rotate the barrel while printing, and it is also often difficult to read indicia such as dose measuring lines and the related numeric values or other markings because they wrap so far around the circumference of the barrel. This problem is accentuated with small-diameter, low-dose syringes where the dosage number is less than "1" and must be preceded by a "0." In such cases, the principal digit identifying the dosage associated with an injection is often not visible when focusing on the volumetric measuring indicia to determine the fluid level within the syringe. These design deficiencies can confuse the user, particularly older users with poor or compromised vision, and contribute to the commission of medical errors.

Other design deficiencies exist with some so-called "safety syringes" that have needle shields or guards that are rotated into place following an injection. Prior to and during an injection, such shields or guards often impede or block a significant portion of the dosage scale and indicia, thereby also contributing to the commission of medical errors.

Other design deficiencies exist with some "safety syringes" having longitudinally extending hubs or other slidable safety elements that increase the overall length of a syringe and contribute to the "dead space" within a syringe. Syringes are needed that protect users, patients and bystanders from accidental needle sticks without also increasing the amount of dead space. A reduction in the amount of dead space within a syringe is necessary to reduce medicinal waste and increase the number of doses available from a single vial.

Other design deficiencies exist with respect to syringes having flat indicia-bearing surfaces configured as sleeves or clips attachable to a syringe barrel. Such syringes require the production of an additional part and contribute to positioning and alignment errors that in turn contribute to dosing errors.

For at least these reasons, low-dose safety syringes with barrels having integrally molded, easily viewable, printable surfaces with factory-applied dosage markings and other indicia are needed, Such syringes will desirably embody low dead space, protect users and patients against accidental needle-stick injuries, and be manufacturable using high speed injection molding methods and equipment that also reduce the per unit cost of such devices.

During the recent and ongoing worldwide pandemic associated with corona virus and other virulent pathogens, increased demand exists for safety syringes that can be made quickly and reliably in various sizes and needle gauges. At the same time, there is increased emphasis on the need for improved syringe designs that can be manufactured more efficiently and inexpensively, with lower material and packaging costs. A syringe is needed that combines a safe and reliable needle-stick protection feature with integrally molded flat and printable indicia display surfaces and a plunger assembly that does not require use of a separate, selectively releasable plunger cap. Also needed is a safety syringe body embodying the foregoing figures that does not require use of a slide for molding undercuts and is instead configured to provide clearance for core pins during injection molding of the syringe body to facilitate use of sixty-four cavity molds with an attendant increase in production capacity and reduction in production costs. Such a safety syringe is disclosed here.

Prior publications disclosing other products with elements said to be within the same technical field include, for example, U.S. Publication No. 2015/0231335 A1 and U.S. Pat. No. 4,946,447.

SUMMARY OF THE INVENTION

A satisfactory embodiment of the subject safety syringe desirably comprises an injection-molded plastic body further comprising a tubular barrel with a needle holder projecting forwardly at its distal end, a transversely projecting finger flange disposed near its proximal end and a cylindrical collar projecting rearwardly from the barrel behind the transversely projecting finger flange, and two longitudinally extending wings contiguous with and projecting upwardly from the barrel in parallel and spaced-apart relation. Each wing has an inwardly facing, integrally molded support and guide rail slidably engaging a cooperatively sized and aligned, longitudinally extending channel of a needle safety shield. Each wing desirably further comprises a substantially flat, outwardly facing surface bearing an array of volumetric marking indicia and dosage numbers disposed proximally to a lower portion of the barrel to be easily readable by a user. The wings each have a proximal end that is contiguous to a side of a window disposed above the barrel in the transverse finger flange. The window, not present in the finger flanges of known prior art devices, is provided to allow insertion and retraction of a core pin between the wings during molding to facilitate more efficient molding and thereby reduce associated production time and product costs.

In some instances in this disclosure, the two wings of the body may be said to project "tangentially" from the barrel. As used in such instances, "tangentially" means that the two elongate wings extend generally upward from opposite sides of the upwardly facing portion of the barrel rather than extending laterally outward from the barrel as with wings used to stabilize some prior art medical devices such as catheter introducers against a body part of a patient. It will be appreciated by those skilled in the art of injection molding such plastic devices as the body of the subject safety syringe that modifications to design criteria such as draft angles and radii of curvature may be needed that do not strictly comport with a mathematical definition of "tangential." Such modifications may be needed, for example, to facilitate molding and reduce stress concentrations along the bases of each wing where they are integrally molded as part of the barrel portion of the body. Similar design modifications may be needed where each wing is integrally molded to its respective guide rail.

A forwardly projecting needle is desirably attached in fixed relation to the needle holder disposed at the distal end of the barrel and a selectively releasable needle cover is desirably provided to protect the needle tip and guard against inadvertent needle-stick injuries or contamination prior to use of the device. The needle cover desirably has a closed distal end and a proximal open end that frictionally engages a forwardly extending nose of the barrel.

The subject invention also desirably comprises a plunger assembly further comprising an elongate handle that is insertable into the barrel through an opening provided by the cylindrical collar projecting rearwardly behind the transverse finger flange of the body. An elastomeric plunger seal disposed at the distal end of the plunger handle slidably engages an inside wall of the tubular barrel. The proximal end of the handle desirably comprises a solid end cap with a forwardly projecting cylindrical collar that fits over, surrounds and slidably engages the rearwardly projecting cylindrical collar of the body. A major portion of the circumference of the forwardly facing cylindrical collar desirably abuts against the rearwardly facing surface portion of the transverse finger flange when the plunger is fully advanced inside the barrel. The forwardly facing cylindrical collar eliminates the need for a separate plunger cap as required by prior art devices to prevent contamination from entering the rear portion of the barrel prior to use.

When the needle cover is installed and the plunger is advanced inside the barrel so that the forwardly projecting cylindrical collar of the plunger abuts against the rearwardly facing surface of the transverse finger flange, the internal, fluid-contacting portions of the syringe are enclosed and protected from contamination whether or not the syringe is also enclosed inside another package. Because of this, the syringes can be assembled and shipped in bulk prior to packaging and sterilization.

The longitudinally extending needle safety shield is disposed above and in parallel alignment with the tubular barrel. The needle safety shield desirably comprises an activation handle with oppositely facing elongate channels that are cooperatively configured and aligned to provide longitudinal sliding engagement with the support and guide rails integrally molded on the inwardly facing surfaces of the wings. The activation handle also desirably comprises an upwardly facing textured touch surface that facilitates the application of manual pressure to initiate forwardly sliding movement of the needle safety shield to reposition a cylindrical needle guard disposed at its distal end forwardly into a position that surrounds the needle tip following use to protect patients and medical personnel from accidental needle sticks and the attendant risk of infection by blood-borne pathogens. The cylindrical needle guard is desirably seated around a forwardly facing cylindrical nose of the barrel during storage and use of the device prior to forward movement of the activation handle. The longitudinal support and guide rails of the wings also desirably cooperate with interference elements, ramps, and shoulder stops molded on the inwardly facing surfaces of the wings to restrict sliding movement of the sliding safety shield relative to the barrel when needed during use of the device, as further described below. A principal advantage of the subject invention is a body configuration having a window through the finger flange that enables the insertion and retraction of core pins to mold the undercut portions of interference elements, ramps and stops of the body without the need for a slide.

Each wing of the body has a base that is contiguous with and projects upwardly from the barrel and comprises an outwardly facing, substantially flat indicia display surface bearing printed dosage markings. The two oppositely disposed wings can have the same or different dosage scales to facilitate volumetric measurements marked in different units. The subject invention is particularly useful with syringes having usable volumes of 1 mL or less, which syringes typically have smaller barrel diameters that cause the volumetric dosage indicia applied to the outside surface to wrap around a greater portion of the circumference of the barrel. According to one embodiment of the invention, pad printing technology (sometimes referred to as "tampography") is used to apply volumetric dosage indicia or other markings to the substantially flat display surface of the syringe. As used here, the term "substantially flat" refers to the general configuration of the relevant surface and can include a slight curvature, draft or minor undulations with comparatively minor raised or recessed portions or features, and particularly, those features attributable to the applied indicia or other markings.

The subject safety syringe embodies needle protection features necessary for safety considerations without the need for and incremental expense of a retractable needle. This embodiment of the invention combines the advantages of flat, printable surfaces having more easily readable dosage indicia with the cost advantages of a simpler but still effective and easy-to-use needle safety device to provide a safe and more affordable solution, particularly for widespread administration of injections associated with vaccines, flu shots, and treatments for persons needing frequent injections (e.g., insulin) to treat various chronic health conditions or for those living in underdeveloped locations. Furthermore, because the dosage markings and indicia are more easily readable by the user, there is less risk of administering an incorrect dosage ("medical error") of a medicinal fluid to a patient and thereby less risk of causing other unintended consequences.

The subject safety syringe desirably embodies wider, substantially flat display surfaces disposed on a medical syringe that cooperate with substantially flat edge portions of the surrounding transverse finger flange to help prevent the syringe from rolling off a tray or other flat surface. The substantially flat surfaces also allow the flange around the barrel to be proportionally narrower as compared to the flanges of conventional syringes having tubular barrels and still provide larger surface areas that are more easily graspable by a user. The oppositely facing, substantially flat wing surfaces also improve stability and the degree of control that can be exercised over the syringe by a user during an injection or other procedure.

The subject safety syringe is also desirably characterized by a low amount of "dead space" between the plunger and needle as compared, for example, to other prior art and competitive syringe configurations. As used here, the term "dead space" refers to the interior volume occupied by medicinal fluid that remains inside a syringe when the plunger is fully advanced inside the barrel. Excessive dead space contributes to medicinal waste during an injection and can also contribute to the formation of undesirable air bubbles inside the fluid chamber of a syringe during aspiration of a fluid. Use of syringes having low dead space can in some cases enable users to obtain an additional dose from each vial of medication. Although the subject syringe is especially useful in administering relatively small doses of a medicinal fluid such as insulin or a vaccine to a user by injection or infusion, the structure and operation of the apparatus is not limited to particular sizes, doses or procedures.

Another embodiment of the invention is disclosed that desirably embodies one and preferably two oppositely facing, substantially flat indicia display surfaces and also embodies a needle safety shield having a needle tip guard that extends circumferentially around the needle and is desirably coaxially aligned with the needle. The needle tip guard is attached or connected to, or unitarily molded together with, an activation handle that slidably engages the body. Suitable rails, ramps, stop shoulders and detents or other similarly effective means are desirably provided as part of the needle safety device and the barrel so that the activation handle can be advanced smoothly and without substantial interference when desired, and will not accidentally retract afterward to expose the needle tip. The needle safety device of this embodiment of the invention eliminates the need for having a needle retraction mechanism, a needle retraction cavity or any transverse sliding movement of the barrel relative to the needle to protect users from accidental needle sticks. Following use of the syringe, the needle tip guard is selectively advanced to protect the user from the forwardly projecting needle tip by applying manual pressure to a touch surface of the activation handle that is located rearwardly of the needle and needle tip guard. The activation handle slidably engages the syringe body and is forwardly slidable relative to the barrel from a first position in which the needle tip is uncovered to a second position in which the needle tip is surrounded and protected against inadvertent needle sticks by the needle tip guard. The needle tip is desirably disposed sufficiently inside the needle tip guard once the needle safety device is fully extended relative to the barrel that someone handling the used syringe will not inadvertently be subjected to a needle stick injury by simply placing a fingertip over the end of the syringe.

In another embodiment of the invention, the barrel and the activation handle comprise cooperatively engageable elements that enable manually actuated and controllable, longitudinally slidable movement of the activation handle relative to the barrel between two predetermined stop positions. The first stop position is a fully retracted use position in which the needle tip guard substantially surrounds the nose. The second stop position is a fully extended post-use position in which the needle tip shield circumferentially surrounds a tip end of the forwardly projecting needle.

In one preferred embodiment of the invention, the forwardly projecting needle is disposed in fixed relation to the nose of the barrel but it will be appreciated upon reading this disclosure that a similarly configured syringe can be made with needles configured to be selectively attachable to the barrel such as by the use of threads or other similarly effective means.

These and other features of the present invention will be better understood from a consideration of the following detailed description of various embodiments and appended claims in conjunction with the accompanying drawings.

BRIEF DESCRIPTION OF THE DRAWINGS

The syringe of the invention is further described and explained in relation to the following drawings wherein:

FIG. 5 is a left side elevation view of the embodiment of FIG. 1;

FIG. 6 is a cross-sectional side elevation view taken along line 6-6 of FIG. 1;

FIG. 7 is the view of FIG. 6 with the plunger partially withdrawn relative to the body;

FIG. 9 is a left side elevation view of FIG. 8;

FIG. 10 is a cross-sectional view taken along line 10-10 of FIG. 8;

FIG. 15 is a top plan view of body 12 of FIG. 3;

FIG. 16 is a top plan view of syringe 10 of FIG. 4;

FIG. 17 is a top plan view of syringe 10 of FIG. 8;

DESCRIPTION OF PREFERRED EMBODIMENTS

Figure 1:
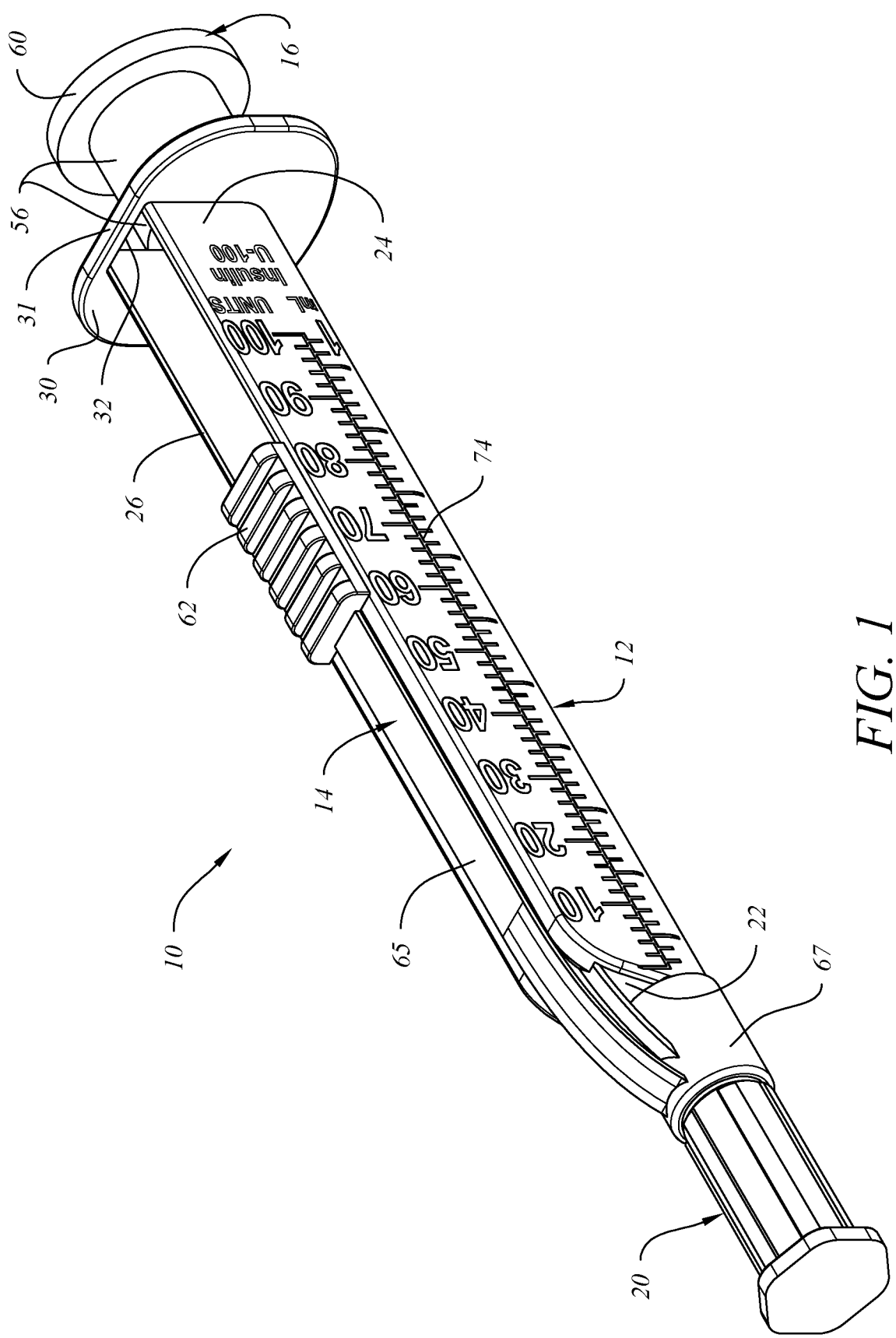
FIG. 1 is a top front perspective view of one embodiment of the invention in which the releasable needle cover is installed in the position in which a plurality of the subject syringes can be packaged, shipped and stored, and the plunger is fully advanced inside the barrel, with the cylindrical collar projecting forwardly of the plunger end cap abutting against a portion of the rearwardly facing surface of the transverse finger flange.
Figure 2:
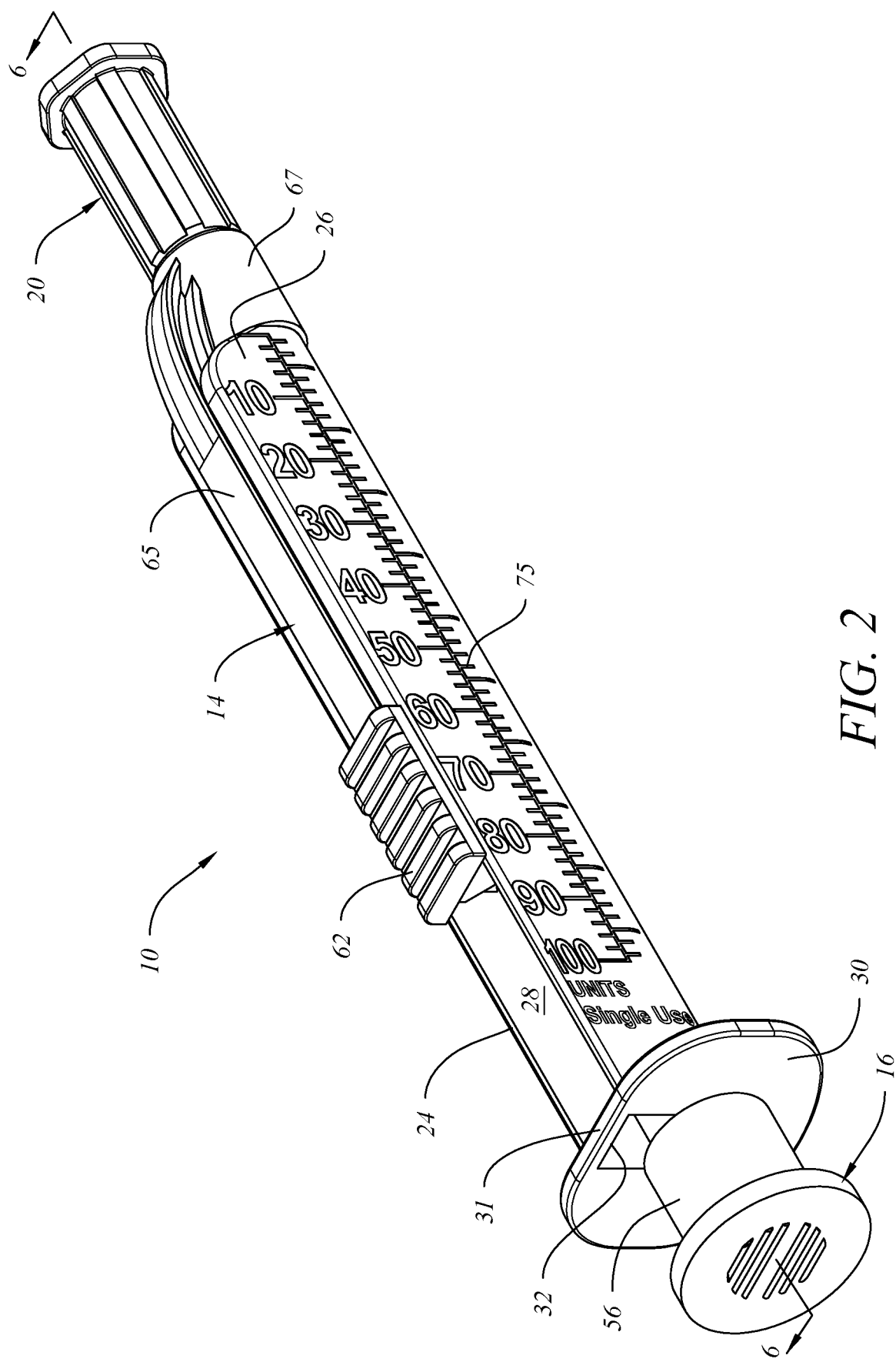
FIG. 2 is a top rear perspective view of the embodiment of FIG. 1.
Figure 3:
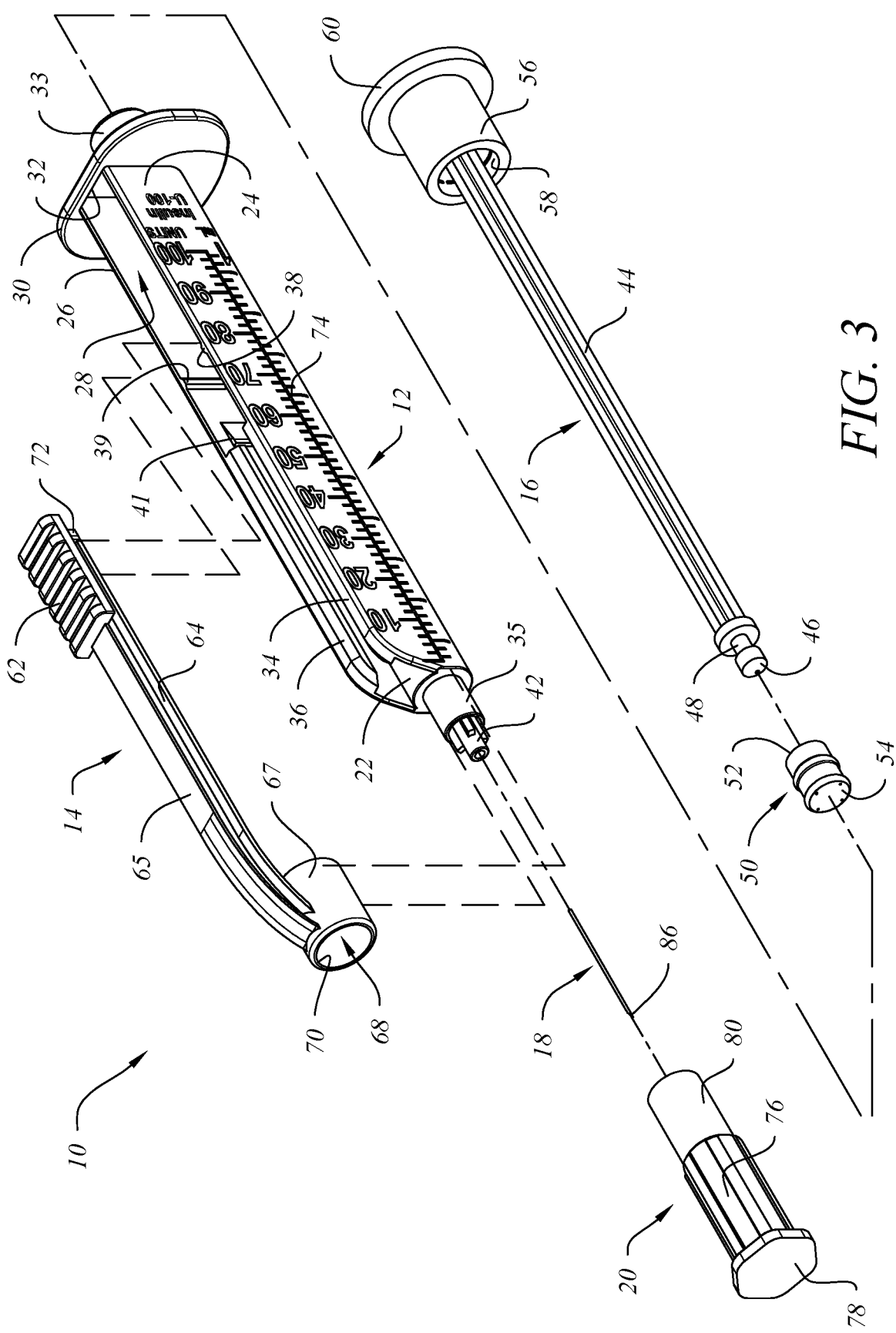
FIG. 3 is an exploded top front perspective view of the embodiment of FIG. 1.

Referring to FIGS. 1-3, safety syringe 10 comprises body 12, needle safety shield 14, plunger assembly 16, needle 18 and removable needle cap 20. Body 12 is desirably molded from a medical grade polymeric material and is sufficiently transparent to permit the liquid level drawn into barrel 22 to be plainly viewed by a user. Body 12 further comprises two upright, substantially parallel, spaced apart wings 24, 26 projecting tangentially above barrel 22 that define an elongate, axially extending space 28 between them. The outwardly facing surfaces of at least one, and preferably both, wings 24, 26 are desirably substantially flat and comprise an array 74, 75 of volumetric measuring indicia applied to display surface.

Arrays 74, 75 can include, for example, at least the Arabic numerals identifying the number of fluid units and the associated principal measurement indicia. It should be appreciated, however, that the accompanying figures of the drawings are for illustrative purposes, are not drawn to scale, and placement of some features such as secondary unit markings can vary from the positions shown. At least a portion of the indicia or markings desirably commences on the substantially flat, outwardly facing display surface of wings 24, 26 and optionally continues for a short distance onto the curved outer wall of barrel 22. Such placement is understood to be within the operational capabilities of conventional pad printing technology that is now readily available to those of ordinary skill in the art.

Finger flange 30 is disposed transversely to barrel 22 and projects outwardly around barrel 22 and the proximal end of wings 24, 26. Finger flange 30 also comprises window 32 having a bottom contiguous with the top surface of barrel 22, sides contiguous with the proximal ends of the inwardly facing surfaces of wings 24, 26 and a top side 31 (FIGS. 1-2) that bridges over the top of window 32 and provides structural support and reinforcement to the upwardly projecting proximal ends of wings 24, 26. Cylindrical collar 33 extends rearwardly from finger flange 30 and provides a rearwardly facing opening that is coaxially aligned and communicates with the inside wall of barrel 22. Body 12 of safety syringe 10 further comprises cylindrical nose 35 projecting forwardly from barrel 22 and needle holder 42 projecting forwardly from cylindrical nose 35.

Needle safety shield 14 desirably comprises elongate activation handle 65 configured to fit between and slidably engage upright wings 24, 26 of body 12. Axially extending channels 64 (FIG. 3) are desirably provided on each side of activation handle 65 to slidably engage cooperative sized and aligned support and guide rails 34, 36 that project inwardly from the inwardly facing surfaces of wings 24, 26, respectively. Needle safety guide further comprises an upwardly facing, desirably textured, touch pad 62 to facilitate the application of digital pressure needed to selectively reposition the slidably engaged needle safety shield from a first position to a second position following use of the device. A forwardly extending portion of activation handle 65 desirably curves downwardly and is attached to an integrally molded, cylindrical needle guard 67 comprising an inside wall 70 defining an interior passage 68. Inside wall 70 of cylindrical needle guard 67 is desirably sized and aligned to slidably engage the outwardly facing surface of cylindrical nose 35 of body 12 when channels 64 of activation handle 65 of needle safety shield 14 receive and slidably engage inwardly facing support and guide rails 34, 36 of body 12 during assembly of safety syringe 10.

Referring to FIG. 3, plunger assembly 16 comprises elongate plunger handle 44 having distal end projection 46 and recessed annular seating surface 48 for elastomeric plunger seal 50. Elastomeric plunger seal 50 further comprises rear collar 52 attachable to distal end projection 46 and forwardly facing end surface 54. Referring to FIGS. 3, 6 and 7, the configuration of elastomeric plunger seal 50 is desirably such that it provides a fluid seal against the inside wall of barrel 22 when the distal end of plunger handle 44 is inserted forwardly through rearwardly projecting cylindrical collar 33 of barrel 22 of body 12 and into sliding engagement with the inside wall of barrel 22. Still referring to FIGS. 3, 6 and 7, the proximal end of plunger handle 44 of plunger assembly 16 is desirably integrally molded with plunger thumb cap 60 having a forwardly projecting cylindrical collar 56 configured to slide forwardly over rearwardly projecting cylindrical collar 33 of barrel 22 when plunger seal 50 and plunger handle 44 are inserted forwardly into barrel 22 during assembly of safety syringe 10 to the configuration depicted in FIGS. 5 and 6. The rear end of needle 18 is insertable into needle holder 42 and attached in fixed relation to the needle holder such as by using an adhesive or another similarly effective, commercially available means.

Referring to FIGS. 5 and 6, safety syringe 10 is fully assembled with needle cap 20 covering forwardly projecting needle 18 having front needle tip 86, and plunger handle disposed fully forward inside barrel 22 so that cylindrical collar 56 projecting forwardly from plunger end cap 60 is abutting against the rearwardly facing surface of finger flange 30. When safety syringe 10 is configured as shown in FIGS. 5 and 6, the inside of barrel 22 is protected against outside contamination without needing a separate plunger cap as needed for use with syringes previously disclosed. Inside surface 58 of cylindrical collar 56 of plunger assembly 16 is desirably configured to slidably engage the outside surface of rearwardly projecting cylindrical collar 33 of body 12.

Figure 4:
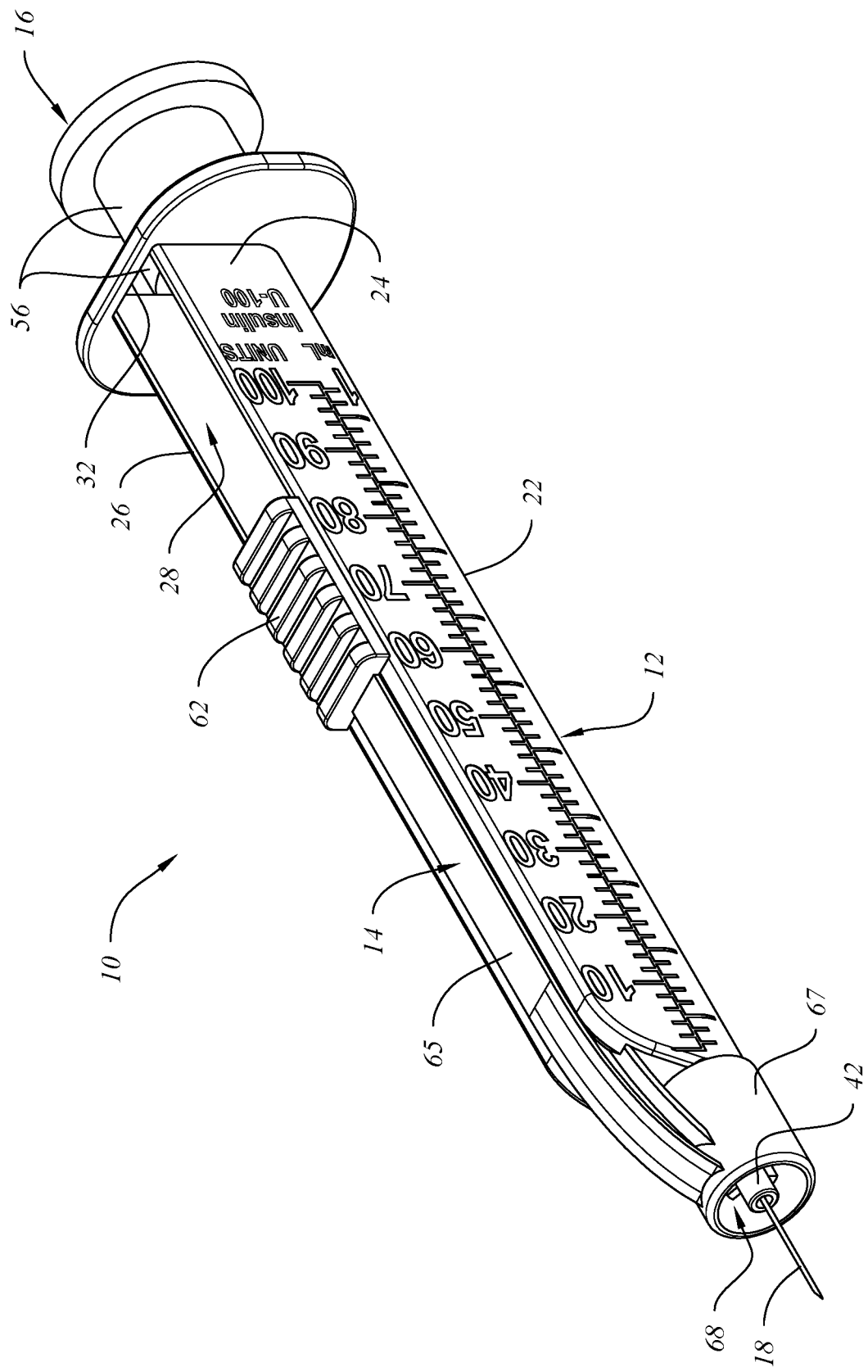
FIG. 4 is a top front perspective view of the embodiment of FIG. 1 with the releasable needle cover removed.
Figure 8:
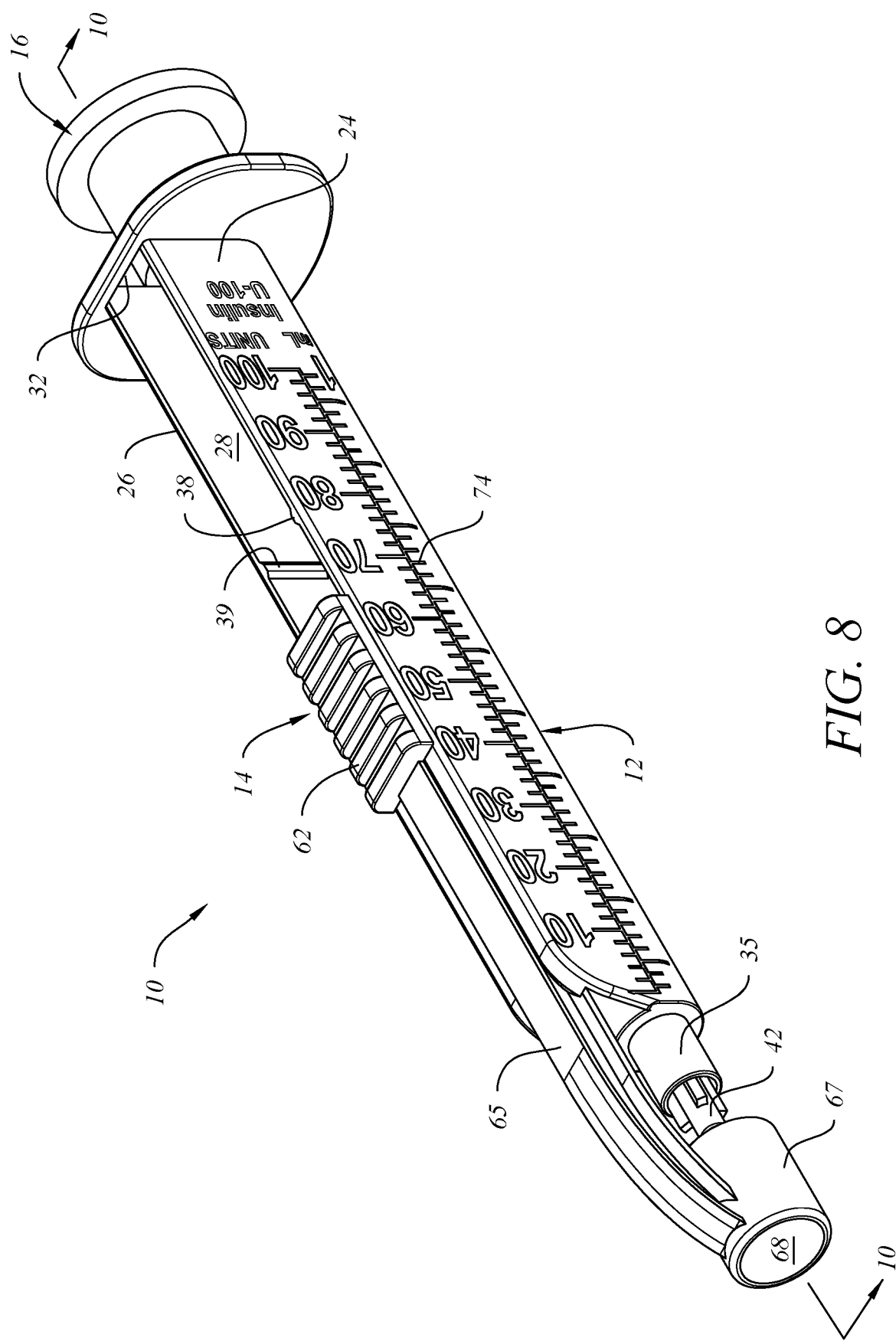
FIG. 8 is the top front perspective view of FIG. 4 with the needle safety shield advanced to cover the forwardly projecting needle.
Figure 11:
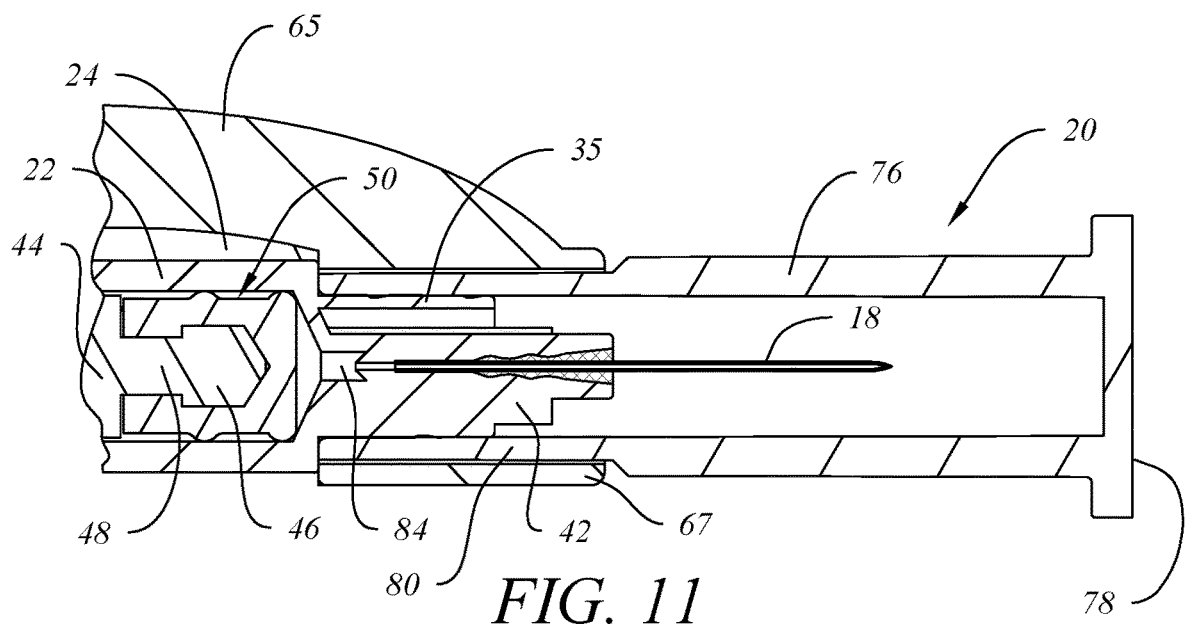
FIG. 11 is an enlarged view of the distal portion of FIG. 6.
Figure 12:
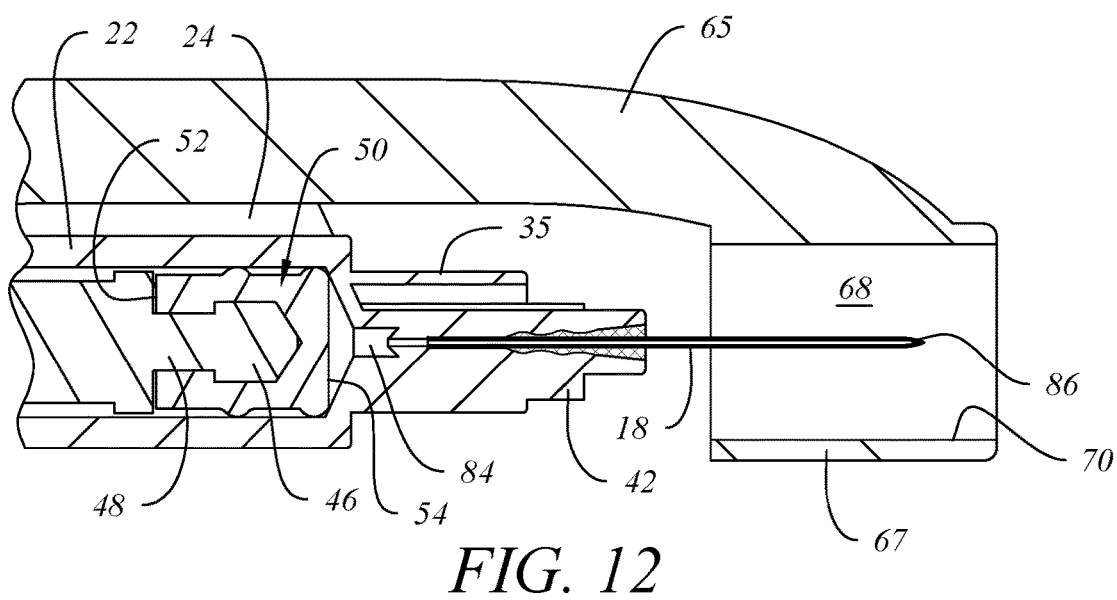
FIG. 12 is an enlarged view of the distal portion of FIG. 10.

Referring to FIG. 4, safety syringe 10 is depicted in the "pre-use" position with needle cap 20 (FIGS. 1-2) removed, needle 18 projecting forwardly from needle holder 42 of barrel 22, and with needle safety shield 14 in its first stop position with cylindrical needle guard 67 disposed in its pre-use position around needle holder 42 and cylindrical nose 35 (FIG. 3) of body 12. Referring to FIGS. 1, 3, 6 and 11, the diametric clearance between the outwardly facing surface of cylindrical nose 35 and the inside wall 70 of cylindrical needle guard 67 is desirably sufficient to allow the rearwardly extending cylindrical portion 80 of selectively removable needle cap 20 to be inserted between them and to frictionally engage the outside surface of cylindrical nose 35. The length of sidewall section 76 of needle cap 20 is desirably sufficient to accommodate needles (such as needle 18) of various lengths and gauges without allowing needle tip 86 (FIG. 6) to engage solid end cap 78 prior to use of safety syringe 10. As seen in FIG. 11, little dead space 84 is present between plunger seal 50 and the proximal end of needle 18 inside needle holder 42 when plunger handle 44 is fully advanced inside barrel 22

Referring next to FIGS. 4 and 7, after needle cap 20 is removed, and with needle safety shield 14 still disposed in its first stop position with cylindrical needle guard 67 still disposed around needle holder 42 and cylindrical nose 35 of body 12, needle 18 can be inserted into a medicine vial and plunger cap 60 of plunger assembly 16 can be withdrawn a desired distance relative to barrel 22 to create a fluid chamber 82 inside barrel 22 to aspirate an injection.

Following the injection, during which plunger handle 44 is again fully advanced inside barrel 22 as shown in FIGS. 8-10 and 12, light manual pressure is desirably applied to upwardly facing touch surface 62 of activation handle 65 of needle safety shield 14 to initiate forward movement of needle safety shield 14 in elongate space 28 relative to barrel 22 and wings 24, 26 of body 12. Activation handle 65 is thereby repositioned to the second stop position in which slide 65 moves forwardly past ramp 40, best seen in FIG. 10, after which activation handle 65 is "locked" in the second stop position and is prevented by abutting contact between the forwardly facing shoulder of ramp 40 and the rearwardly facing end surface 72 of activation handle 65. When this occurs, cylindrical needle guard 67 is moved forwardly into a position where needle tip 86 of needle 18 is disposed inside cylindrical space 68 and protects needle tip 86 from causing an accidental needle stick injury to a user, patient, bystander or subsequent handler of safety syringe 10.

Figure 13:
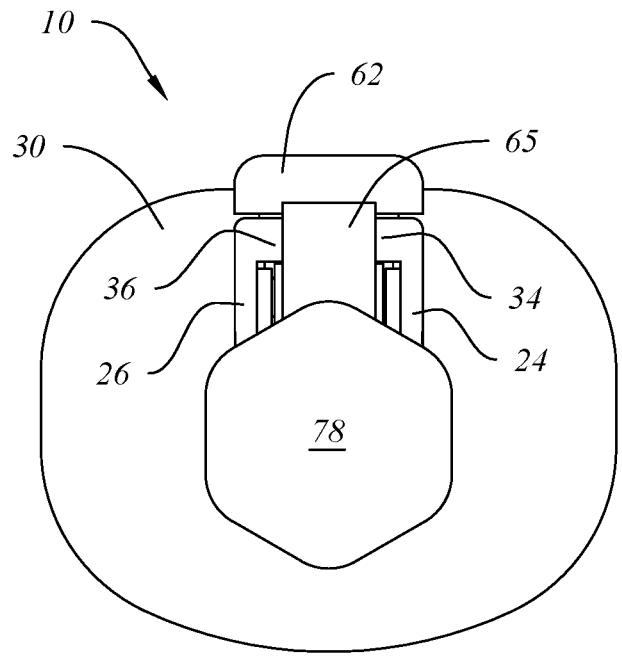
FIG. 13 is a front elevation view of FIG. 1.
Figure 14:
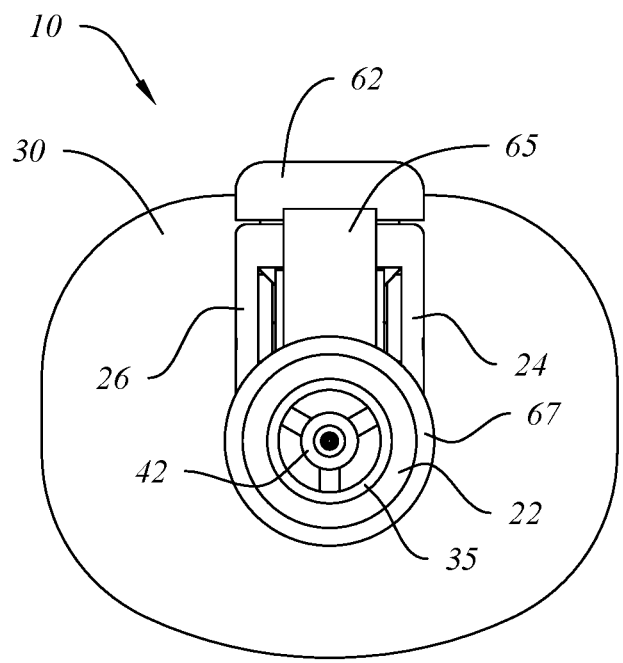
FIG. 14 is a front elevation view of FIG. 4.

Referring to FIGS. 13 and 14, a front elevation view of safety syringe 10 shows wings 24, 26, support and guide rails 34, 36, barrel 22, end wall 78 of needle cap 20, upwardly facing touch pad 62 and cylindrical needle guard 67 of activation handle 65, needle holder 42, cylindrical nose 35 and transverse finger flange 30. In FIG. 13, needle cap 20 is in place and in FIG. 14, the needle cap is removed.

Referring to FIG. 15, which is a top plan view of body 12, needle holder 42 and cylindrical nose 35 project forwardly from barrel 22 and cylindrical collar 33 projects rearwardly behind finger flange 30. Top side 31 of window 32 (FIG. 3) is visible and bridges and supports the top of wings 24, 26, which are disposed on opposite sides of axially extending space 28 disposed above barrel 22. Support and guide rails 34, 36 project inwardly from the inwardly facing walls of wings 24, 26, respectively. Referring to FIGS. 3 and 15-16, opposed interference elements 38, 39 are desirably integrally molded and configured to frictionally engage and provide slight resistance to forward sliding movement of needle safety shield 14 (FIG. 16) while needle safety shield 14 is disposed in the first stop position and cylindrical needle guard 67 is seated around cylindrical nose 35 and needle holder 42 of body 12. Referring to FIGS. 16-17, when digital pressure is applied forwardly to upwardly facing touch surface 62 of activation handle 65 of needle safety shield 14 following an injection, needle safety shield slides 14 forwardly past interference elements 38, 39 and past ramps 40, 41 (FIG. 17) to a second stop position (also referred to as a "safe" position) where cylindrical needle guard 67 surrounds tip 86 of needle 18 (visible in FIG. 16). Referring to FIGS. 10 and 17, once needle safety shield 14 reaches the second stop position, any rearward movement of needle safety shield 14 relative to barrel 22 and needle 18 is desirably blocked by the facing and abutting contact between rearwardly facing shoulder 72 of needle safety shield 14 and the forwardly facing shoulders of ramps 40, 41. This abutting contact prevents cylindrical needle guard from again exposing needle tip 86 after needle safety shield 14 has been moved to the second stop position following use of safety syringe 10.

Figure 26:
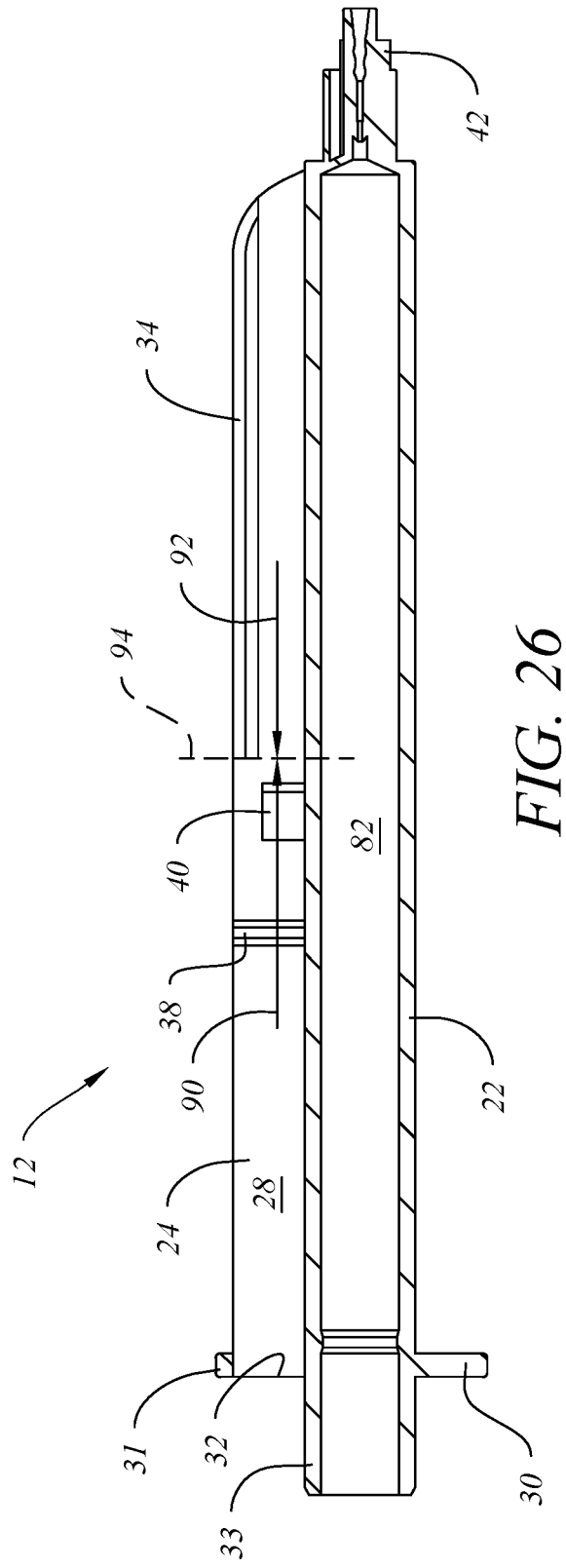
FIG. 26 is a cross-sectional side elevation view of the body as shown in FIG. 15.

Referring to FIG. 26, which is a longitudinal cross-sectional side elevation view of body 12 as shown in FIG. 15, arrows 90, 92 are shown for illustrative purposes to indicate the direction and extent to which oppositely disposed injection molding core pins are insertable into space 28 between wings 24, 26 and a desired position of core pin stop line 94. This facilitates integral molding of longitudinally extending support and guide rails 34, 36, interference elements 38, 39 and ramps 40, 41 projecting inwardly from the inwardly facing surfaces of wings 24, 26 without the need for a slide. This in turn facilitates the use of higher cavity molds, increases manufacturing efficiency, and lowers production costs for barrel 12 and safety syringe 10 (FIG. 1).

Figure 18:
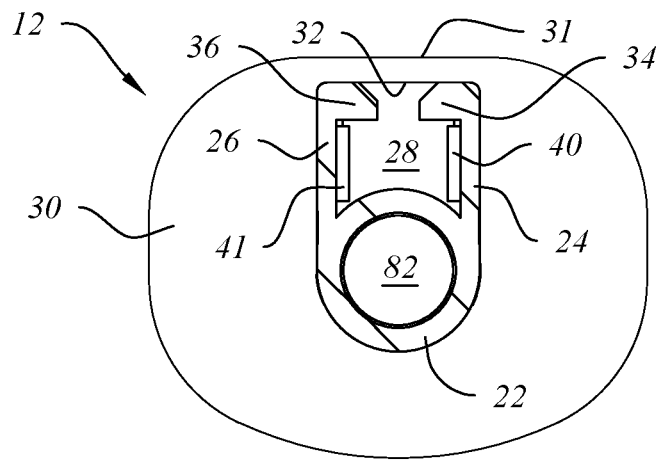
FIG. 18 is a cross-sectional elevation view taken along line 18-18 of FIG. 15.

FIG. 18 is a cross-sectional view of barrel 12 taken along line 18-18 of FIG. 15 and further illustrates how support and guide rails 34, 36 project inwardly from wings 24, 26 into axially extending space 28 disposed above barrel 22 and also shows the facing surfaces on the front of ramps 40, 41 disposed forwardly of window 32 of transverse finger flange 30. The void shown inside barrel 22 is the space that becomes fluid chamber 82 following the insertion of a plunger assembly inside the barrel.

Figure 19:
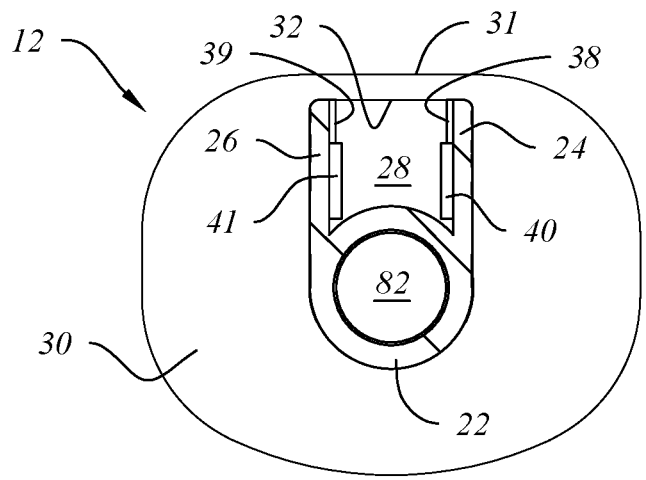
FIG. 19 is a cross-sectional elevation view taken along line 19-19 of FIG. 15.

FIG. 19 is a cross-sectional view of barrel 12 looking rearwardly behind the support and guide rails and showing space 28 between wings 24, 26 with a view of window 32 of finger flange 30 that is obstructed only by oppositely disposed interference elements 38, 39 and the forwardly facing surfaces of ramps 40, 41. Top side 31 of window 32 provides structural support and integrity between the portion of wings 24, 26 that is contiguous with window 32 in finger flange 30.

Figure 20:
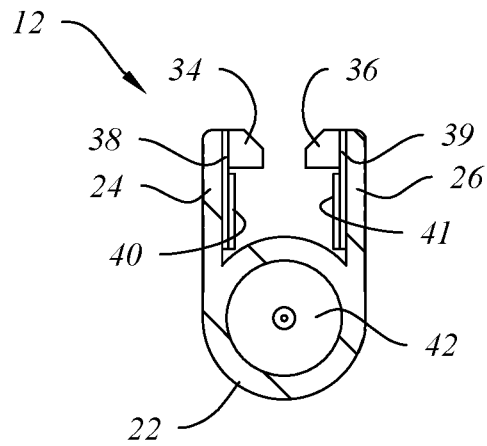
FIG. 20 is a cross-sectional elevation view taken along line 20-20 of FIG. 15.

FIG. 20 is a forwardly looking cross-sectional elevation view taken forwardly of finger flange 30 along line 20-20 of FIG. 15 and shows wings 24, 26, interference elements 38, 39, ramps 40, 41 and the proximal end of needle holder 42 disposed forwardly of barrel 22.

Figure 21:
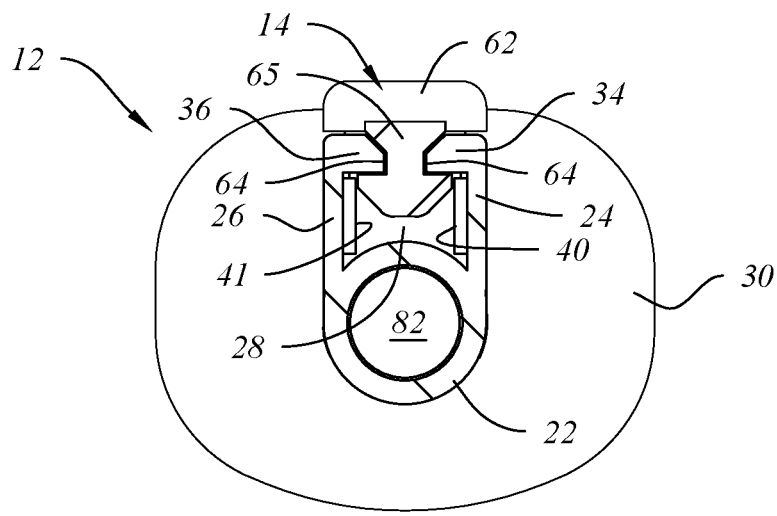
FIG. 21 is a cross-sectional elevation view taken along line 21-21 of FIG. 16.

FIG. 21 is a rearwardly facing cross-sectional elevation view taken along line 21-21 of FIG. 16 and shows the sliding engagement between support and guide rails 34, 36 of needle safety shield 14 and longitudinal channels 64 disposed on opposite sides of activation handle 65. Upwardly projecting touch surface 62 of needle safety shield 14 projects is visible above activation handle 65 and forwardly facing surfaces of ramps 40, 41 are visible within space 28.

Figure 22:
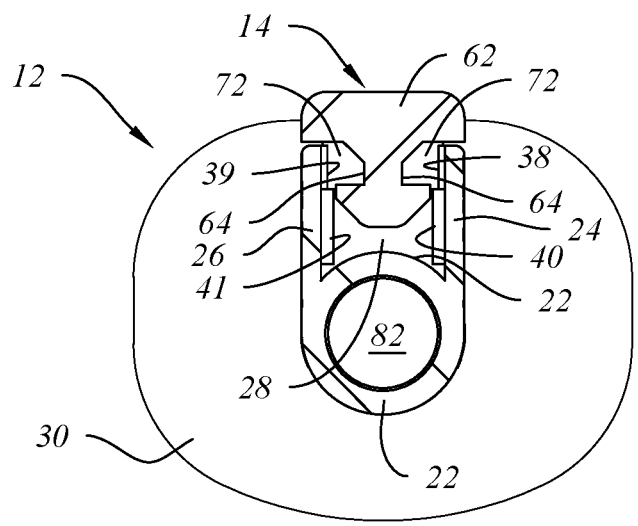
FIG. 22 is a cross-sectional elevation view taken along line 22-22 of FIG. 16.

FIG. 22 is another rearwardly facing cross-sectional elevation view taken along line 22-22 of FIG. 16 and shows that portion of the assembled body 12 and needle safety shield 14 as viewed through upwardly facing touch surface 62 when needle safety shield 14 is in the first stop position relative to barrel 22 of safety syringe 10.

Figure 23:
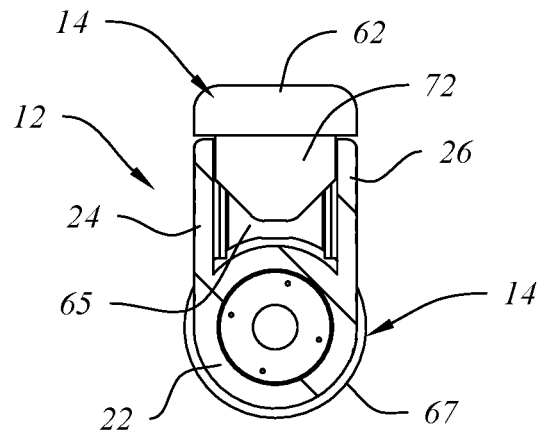
FIG. 23 is a cross-sectional elevation view taken along line 23-23 of FIG. 16.

FIG. 23 is a forwardly facing cross-sectional elevation view taken along line 23-23 of FIG. 16 forwardly of finger flange 30 and from behind needle safety shield 14. FIG. 23 shows proximal end surface 72 of activation handle 65 and the underside of activation handle 65 that curves downwardly to join cylindrical needle guard 67.

Figure 24:
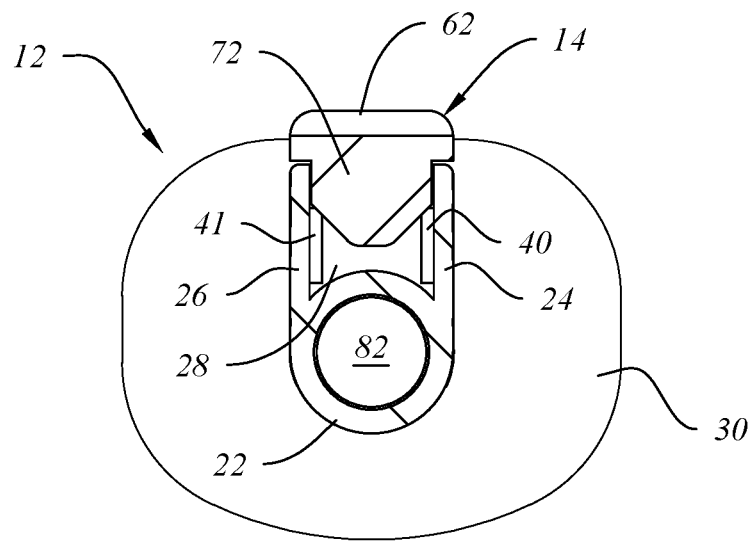
FIG. 24 is a cross-sectional elevation view taken along line 24-24 of FIG. 17.

FIG. 24 is a rearwardly facing cross-sectional elevation view taken along line 24-24 of FIG. 17 after needle safety shield 14 has been moved forwardly from the first stop position to the second stop position with the cylindrical needle guard moved forwardly to protect needle tip 86 of needle 18 (FIG. 16). FIG. 24 is taken through end wall 72 of activation handle and looks rearwardly at a top portion of touch surface 62.

Figure 25:
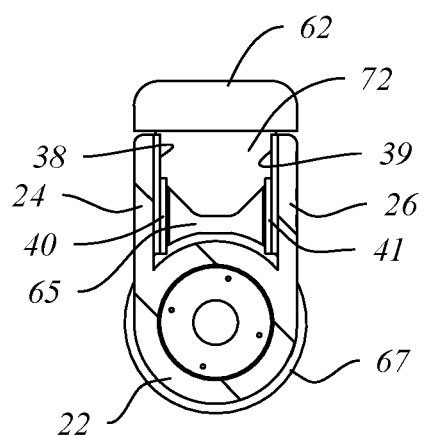
FIG. 25 is a cross-sectional elevation view taken along line 25-25 of FIG. 17.

FIG. 25 is a forwardly looking cross-sectional elevation view taken forwardly of finger flange 30 along line 25-25 of FIG. 17 and shows wings 24, 26, interference elements 38, 39, and the proximal end 72 of needle safety shield 14 blocked by a portion of ramps 40, 41.

It will become apparent to those of ordinary skill in the art upon reading this specification in relation to the accompanying drawings that various other modifications and alterations can also be made to the embodiments disclosed here, and it is intended that the scope of the invention be limited only by the broadest interpretation of the appended claims to which the inventors are legally entitled.

We claim:

1. A safety syringe for medical use, comprising:
   an injection-molded plastic body comprising a tubular barrel, a cylindrical nose projecting forwardly from the barrel, a needle holder projecting forwardly from the cylindrical nose, a finger flange projecting transversely from the barrel, a cylindrical collar projecting rearwardly from the finger flange, and two substantially parallel, spaced-apart wings extending forwardly from the finger flange and projecting tangentially from the barrel, wherein the finger flange comprises a window formed between the two substantially parallel, spaced-apart wings;
   a needle coupled to and projecting forwardly from the needle holder and comprising a needle tip;
   a plunger assembly comprising a plunger handle, a distal end of the plunger handle having an elastomeric plunger seal insertable into the barrel through a rearwardly facing opening in the cylindrical collar to slidably engage an inside wall of the barrel, and a proximal end of the plunger handle having a thumb cap with a forwardly projecting cylindrical collar that slides forwardly over the cylindrical collar of the body and abuts against a rearwardly facing surface of the finger flange when the plunger assembly is fully advanced inside the barrel; and
   a needle safety shield comprising an activation handle disposed between and slidably engaging the wings and an upwardly facing touch surface that facilitates an application of manual pressure by a user to initiate forward sliding movement of the needle safety shield relative to the body to selectively reposition a cylindrical needle guard disposed at a forward end of the needle safety shield from a first position surrounding the cylindrical nose of the body during use of the safety syringe to a second position guarding the needle tip following the use of the safety syringe.

2. The safety syringe of claim 1, wherein each wing comprises an inwardly projecting, longitudinally extending guide rail that is slidably engageable with the activation handle of the needle safety shield.

3. The safety syringe of claim 2, wherein each guide rail is cooperatively sized and aligned and slidably engageable with a channel disposed on an adjacent side of the activation handle of the needle safety shield.

4. The safety syringe of claim 1, wherein the window is cooperatively sized and aligned with the activation handle of the needle safety shield.

5. The safety syringe of claim 1, wherein the window has a side that is contiguous with a proximal end portion of each upright wing of the body.

6. The safety syringe of claim 5, wherein the window has a top section that bridges and provides structural support between the wings of the body.

7. The safety syringe of claim 2, wherein each guide rail is integrally molded as part of the wing from which it projects.

8. The safety syringe of claim 1, wherein at least one wing of the body comprises a substantially flat, outwardly facing surface bearing indicia related to volumetric measurements of a fluid disposed inside the syringe.

9. The safety syringe of claim 8, wherein each wing of the body comprises a substantially flat, outwardly facing surface bearing indicia related to volumetric measurements of a fluid disposed inside the syringe.

10. The safety syringe of claim 2, wherein the guide rails cooperate with interference elements molded on inwardly facing surfaces of the wings of the body to restrict sliding movement of the needle safety shield relative to the barrel.

11. The safety syringe of claim 10, wherein the interference elements each include a ramp having a forwardly facing stop shoulder.

12. The safety syringe of claim 11, wherein the needle safety shield comprises a rearwardly facing stop surface that engages the forwardly facing stop shoulders of the ramps to prevent subsequent rearward movement of the needle safety shield relative to the body following repositioning of the cylindrical needle guard to the second position.

13. The safety syringe of claim 8, wherein the indicia related to volumetric measurements of a fluid disposed inside the syringe extends onto a curved outer wall of the barrel.

14. The safety syringe of claim 9, wherein the indicia related to volumetric measurements of a fluid disposed inside the syringe extends onto a curved outer wall of the barrel.

15. The safety syringe of claim 1, wherein the wings of the body extend from the finger flange along the barrel to the cylindrical nose of the body.

16. The safety syringe of claim 15, wherein the upwardly facing touch surface of the needle safety shield extends laterally over the wings of the body.

17. The safety syringe of claim 1, wherein the activation handle curves to attach to the cylindrical needle guard disposed at the forward end of the needle safety shield.

18. A safety syringe for medical use, comprising:
   a body comprising a tubular barrel, a cylindrical nose projecting forwardly from the barrel, a needle holder projecting forwardly from the cylindrical nose, a finger flange projecting transversely from the barrel, a cylindrical collar projecting rearwardly from the finger flange, and two substantially parallel, spaced-apart wings extending forwardly from the finger flange along the barrel and projecting tangentially from the barrel, wherein the finger flange comprises a window formed between the two substantially parallel, spaced-apart wings, and wherein each of the wings comprises an inwardly projecting, longitudinally extending guide rail;
   a needle coupled to and projecting forwardly from the needle holder and comprising a needle tip;
   a plunger assembly comprising a plunger handle, a distal end of the plunger handle having an elastomeric plunger seal insertable into the barrel through a rearwardly facing opening in the cylindrical collar to slidably engage an inside wall of the barrel, and a proximal end of the plunger handle having a thumb cap; and
   a needle safety shield comprising an activation handle having channels disposed on opposing sides, a needle guard disposed at a forward end of the activation handle, and an outwardly facing touch surface disposed at a rear end of the activation handle, wherein the channels of the activation handle slidably engage the inwardly projecting, longitudinally extending guide rails of the wings during movement of the needle safety shield between a first position where the needle guard surrounds the cylindrical nose of the body and a second position where the needle guard circumferentially surrounds the needle to protect a user from inadvertent contact with the needle tip.

19. The safety syringe of claim 18, wherein the needle safety shield is positioned in the first position during use of the safety syringe and in the second position after use of the safety syringe.

20. The safety syringe of claim 18, wherein the window comprises sides that are contiguous with proximal end portions of each upright wing of the body, and wherein the window has a top section that bridges and provides structural support between the wings of the body.

* * * * *